United States Patent [19]

Driscoll et al.

[11] 4,146,622

[45] Mar. 27, 1979

[54] AZIRIDINYL QUINONE ANTI-TRANSPLANTED TUMOR AGENTS

[75] Inventors: John S. Driscoll; A. Hameed Khan, both of Rockville; Feng-te Chou, Bethesda, all of Md.

[73] Assignee: The Government of the United States, Washington, D.C.

[21] Appl. No.: 758,812

[22] Filed: Jan. 12, 1977

[51] Int. Cl.² .................. A61K 31/33; A61K 31/535; A61K 31/495; A61K 31/40

[52] U.S. Cl. .............................. 424/244; 424/248.56; 424/250; 424/274

[58] Field of Search ................... 424/244, 248.56, 250, 424/274

[56] References Cited

U.S. PATENT DOCUMENTS

| | | | |
|---|---|---|---|
| 2,802,001 | 8/1957 | Marxev | 424/244 |
| 2,913,453 | 11/1959 | Petersen et al. | 260/239 EQ |
| 3,211,721 | 10/1965 | Marxev | 260/239 EQ |
| 3,462,531 | 8/1969 | Jaques et al. | 424/244 |
| 3,631,026 | 12/1971 | Nakao et al. | 424/244 |

OTHER PUBLICATIONS

Chou et al., J. of Med. Chem., 1976, vol. 19, No. 11, pp. 1302-1308.

*Primary Examiner*—Jerome D. Goldberg
*Attorney, Agent, or Firm*—Holman & Stern

[57] ABSTRACT

The use of aziridinyl quinones as antitumor agents against transplanted tumors in mice is disclosed. A compound which has been found to be particularly effective is the compound 2,5-diaziridinyl-3,6-bis (carboethoxyamino)-1,4-benzoquinone. Treatment is described in connection with several transplanted mouse tumor test systems including various forms of leukemia, for example, as well as B16 melanoma, Lewis lung carcinoma, and the ependymoblastoma brain tumor system.

25 Claims, No Drawings

AZIRIDINYL QUINONE ANTI-TRANSPLANTED TUMOR AGENTS

BACKGROUND AND SUMMARY OF THE INVENTION

The present invention relates to the use of aziridinyl quinones as potential central nervous system antitumor agents. More particularly, the present invention is concerned with a diaziridinyldi(carboethoxyamino)benzoquinone which has been found to have significant activity as a central nervous system antitumor agent against transplanted tumors in mice.

A recent analysis of murine antitumor test data has indicated that the aziridinylquinones, as a family, possess significant activity against lymphoid leukemia L1210 as well as other transplanted mouse tumor test systems. While the L1210 results were all obtained on an intraperitoneally (IP) implanted tumor, the molecular properties of the compounds appeared to fit some of the requirements suggested by Rall and Zubrod in *Annu. Rev. Pharmacol.*, 2, 109 (1962) as important for central nervous system (CNS) penetration. Subsequent testing of these compounds in several intracerebral (IC) transplanted mouse tumor systems indicated that the aziridinylquinones possessed substantial IC antitumor activity.

However, a major problem associated with almost all of the antitumor active aziridinylquinones is the very low aqueous solubility of the compounds. This has greatly complicated the preparation of a suitable parenteral dosage form. The present invention is concerned with aziridinylquinones having optimized properties as CNS antitumor agents against transplanted tumors in mice. Emphasis has been placed on the study of the effect of nonionic functional groups, since ionic materials have difficulty penetrating the blood-brain barrier.

The chemistry used in the synthesis of the compounds of interest is based mainly on the reactions of tetrachlorobenzoquinone, also known as chloranil, and its tetrafluoro analog, fluoranil. Chloranil may be obtained in a well known manner from phenol, p-chlorophenol or p-phenylenediamine by treatment with potassium chlorate and hydrochloric acid. Fluoranil is prepared from chloranil by reaction with calcium fluoride at elevated temperatures.

DESCRIPTION OF THE PREFERRED EMBODIMENTS

The reaction of chloranil with aziridine and its analogs was carried out to produce the disubstituted compounds Nos. 2 and 3, as shown in Table I by a procedure as set forth in British Patent No. 762,723. Compound 4, 2,5-dichloro-3,6-diaziridinyl-1,4-benzoquinone, was converted to the corresponding ethyl-(No. 5) and propyl mercapto (No. 6) derivatives. It was possible to replace all the chlorine atoms in chloranil with ethylmercapto groups, No. 7. Chloranil also reacted with the sodium salt of urethane to produce No. 8, a key intermediate. Attempts to react chloranil with methyl carbamate, urea, thiourea, and diethyl malonate in a similar manner were not successful. The diaziridinylbenzoquinone urethanes, Nos. 9–11, were prepared from No. 8.

TABLE I.
PHYSICAL AND CHEMICAL DATA

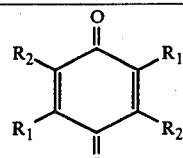

| No. | R$_1$ | R$_2$ | Mp, °C | Yield, % | λ$_{max}$ CH$_3$OH (log ε) | Mol formula | Analyses$^f$ |
|---|---|---|---|---|---|---|---|
| 2 | MeAz$^a$ | Cl | 155$^b$ | 52 | 347 (4.24) | C$_{12}$H$_{12}$Cl$_2$N$_2$O$_2$ | C, H, N, Cl |
| 3 | Me$_2$Az | Cl | 200 | 15 | 362 (4.30) | C$_{14}$H$_{16}$Cl$_2$N$_2$O$_2$ | C, H, N, Cl |
| 5 | Az | SC$_2$H$_5$ | 135$^c$ | 33 | 340 (6.18) | C$_{14}$H$_{18}$N$_2$O$_2$S$_2$ | C, H, N, S |
| 6 | Az | SC$_3$H$_7$ | 159 | 44 |  | C$_{16}$H$_{22}$N$_2$O$_2$S$_2$ | C, H, N, S |
| 7 | SC$_2$H$_5$ | SC$_2$H$_5$ | 88 | 13 |  | C$_{14}$H$_{20}$O$_2$S$_2$ | C, H, S |
| 8 | NHCOOC$_2$H$_5$ | Cl | 220 | 27 | 317 (4.06) | C$_{12}$H$_{12}$Cl$_2$N$_2$O$_6$ | C, H, N, Cl |
| 9 | Az | NHCOOC$_2$H$_5$ | 230$^d$ | 68 | 340 (4.17) | C$_{16}$H$_{20}$N$_4$O$_6$ | C, H, N |
| 10 | MeAz | NHCOOC$_2$H$_5$ | 198 | 89 |  | C$_{18}$H$_{24}$N$_4$O$_6$ | C, H, N |
| 11 | Me$_2$Az | NHCOOC$_2$H$_5$ | 175 | 22 | 355 (4.23) | C$_{20}$H$_{30}$N$_4$O$_6$ | C, H, N |
| 12 | NHCH$_2$CH$_2$Cl | NHCOOC$_2$H$_5$ | 215 | 68 | 340 (4.40) | C$_{16}$H$_{22}$Cl$_2$N$_4$O$_6$ | C, H, N, Cl |
| 15 | Az | Br | 181$^e$ | 47 | 347 (4.15) | C$_{10}$H$_8$Br$_2$N$_2$O$_2$ | C, H, N |
| 16 | MeAz | Br | 160 | 69 | 357 (4.24) | C$_{12}$H$_{12}$Br$_2$N$_2$O$_2$ | C, H, N |
| 17 | Me$_2$Az | Br | 210 | 16 | 362 (4.26) | C$_{14}$H$_{18}$Br$_2$N$_2$O$_2$ | C, H, N |
| 18 | NHNH$_2$ | Cl | 198 | 78 | 330 (3.59) | C$_6$H$_8$Cl$_4$N$_4$O$_2$ | C, H, N, Cl |
| 19 | NH$_2$ | Cl | 360 | 72 |  | C$_6$H$_4$Cl$_2$N$_2$O$_2$ | C, H, N, Cl |
| 21 | Me$_2$Az | NHCOCH$_3$ | 205 | 73 |  | C$_{18}$H$_{26}$N$_4$O$_4$ | C, H, N |
| 22 | NCHOC$_2$H$_5$ | Cl | 148 | 76 | 320 (5.40) | C$_{12}$H$_{12}$Cl$_2$N$_2$O$_4$ | C, H, N, Cl |

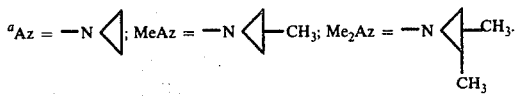

$^b$Lit. mp 182°.
$^c$Lit. mp 134°.
$^d$Lit. mp 250°.
$^e$Lit. mp 178°.
$^f$Analyses indicated were determined experimentally to be within ± 0.4% of theoretically calculated values.

The aziridine rings of No. 9 were opened with HCl to give the bis (2-chloroethylamino) derivative, No. 12. The preparation of compound No. 9 is as follows:

2,5-Diaziridinyl-3,6-bis (carboethoxyamino)-1,4-benzoquinone, No. 9. General Procedure for Nos. 10, 11, and 21. A solution of No. 8 (1.5 g, 0.004 mol) in tetrahydrofuran (THF) (60 ml) was added dropwise to a stirred solution of ethylenimine (1.0 ml, 0.03 mol) and triethylamine (2.5 ml) in THF (20 ml). After the addition was complete (0.5 hr), the reaction mixture was stirred at room temperature overnight, about 16 hrs. Excess solvent was removed in vacuo and the resulting reddish-brown solid was washed with ice-cold water and dried over KOH pellets in vacuo. Recrystallization from ethanol gave 1.06 g (68%) of orange needles: mp 230° dec (lit. mp 250°). Compound No. 9 is known in the patent literature, being disclosed in U.S. Pat. No. 2,913,453.

The dibromodiaziridinylbenzoquinones, Nos. 15-17 as shown in Table I, were prepared in a three-step synthesis starting from benzoquinone. Reaction of 1,4-benzoquinone with anhydrous zinc chloride in methanol gave No. 13, 2,5-dimethoxy-1,4-benzoquinone, which was brominated to yield No. 14, 2,5-dibromo- 3,6-dimethoxy-1,4-benzoquinone. Aziridine replaced the methoxy groups rather than the halogen atoms in accordance with the reported relative reactivities of tetrasubstituted benzoquinones.

Ammonia and hydrazine reacted with chloranil to produce Nos. 18 and 19. These compounds were unreactive toward other nucleophiles because of ring deactivation by the electron-donating amino groups. Reactivation of the ring by acetylation produced No. 20, 2,5-dichloro-3,5-acetylamino-1,4-benzoquinone, which then reacted with 2,2-dimethylaziridine to give No. 21. The monomethyl and unsubstituted aziridine analogs of No. 21 had previously been prepared and tested. Compound No. 19 also reacted with diethoxymethyl acetate to give No. 22 but this compound was unreactive toward aziridine. Physical and chemical data for these compounds are summarized in Table I.

So far as antitumor activity against transplanted mouse tumor test systems is concerned, chloranil itself, as well as compounds Nos. 4, 14, 19, and 20 had had prior testing and were inactive in the L1210 system. Compounds Nos. 2, 3, 5-12, 15-18, 21, and 22 were tested during this study in the lymphoid leukemia L1210 system by standard NCI protocols on the Q4D (day 1, 5, 9 with a total of 3 injections) and the QD1-9 (day 1-9 with a total of 9 injections) treatment schedules. Among these compounds, only compound No. 9 was active with an increase in life span (ILS) >25%, as shown in Table II.

The optimum dose and activity (%ILS) for No. 9 on the Q4D schedule was 6.25 mg/kg (54%). Compound No. 9 had greater L1210 activity on the QD1-9 schedule, however (Table II). The compound had an aqueous solubility of approximately 0.5 mg/ml. Assuming an active dose range of 2.5-10 mg per dose since only 20 ml of water would be required to dissolve 10 mg. of No. 9, the solubility of this compound appears to be in the acceptable range.

TABLE II.

ANTITUMOR ACTIVITY[a] OF COMPOUND 9

| 210 lymphoid leukemia[b] | | | | P388 lymphocytic leukemia[b] | | | | B16 melanocarcinoma[b] | | | | Lewis lung carcinoma[c] | | | |
|---|---|---|---|---|---|---|---|---|---|---|---|---|---|---|---|
| Expt. no. | Dose[d] | ILS[e] | I − C[f] | Expt. no. | Dose | ILS | T − C | Expt no. | Dose | ILS | T − C | Expt no. | Dose | ILS | T − C |
| 42 | 12.50 | T[g] | −5.0 | 4323 | 3.12 | 12 | −3.6 | 267 | 625 | T | −3.5 | 8 | 4.00 | T | −0.1 |
|  | 6.25 | 27 | −4.1 |  | 1.56 | 138 | −2.4 |  | 3.12 | 58 | −1.9 |  | 2.00 | 38 | +0.3 |
|  | 3.12 | 113 | −3.2 |  | 0.78 | 111 | −2.4 |  | 1.56 | 38 | −1.2 |  | 1.00 | 27 | −0.1 |
|  |  |  |  |  |  |  |  |  | 0.78 | 36 | −1.4 |  |  |  |  |
| 40 | 4.60 | 0 | −4.6 | 4328 | 6.25 | T | −6.1 | 284 | 6.25 | T | −4.4 | 9 | 4.00 | T | +1.7 |
|  | 3.12 | 28 | −3.1 |  | 3.12 | 27 | −4.1 |  | 3.12 | 43 | −2.7 |  | 2.00 | 34 | +1.6 |
|  | 2.00 | 101 | −3.6 |  | 1.56 | 135 | −4.0 |  | 1.56 | 44 | −3.6 |  | 1.00 | 0 | +2.4 |
|  |  |  |  |  | 0.78 | 99 | −2.1 |  | 0.78 | 13 | −2.2 |  |  |  |  |
| 62 | 1.30 | 60 | −2.3 | 4387 | 3.12 | 0 | −3.4 | 285 | 6.25 | T | −3.5 |  |  |  |  |
|  | 0.88 | 32 | −1.4 |  | 1.56 | 112 | −2.1 |  | 3.12 | 70 | −1.2 |  |  |  |  |
|  |  |  |  |  | 0.78 | 112 | −1.4 |  | 1.56 | 58 | −2.7 |  |  |  |  |
|  |  |  |  |  |  |  |  |  | 0.78 | 36 | −1.1 |  |  |  |  |
| 95 | 4.60 | 51 | −3.9 |  |  |  |  |  |  |  |  |  |  |  |  |
|  | 3.12 | 169 | −4.1 |  |  |  |  |  |  |  |  |  |  |  |  |
|  | 2.00 | 125 | −3.8 |  |  |  |  |  |  |  |  |  |  |  |  |

[a]Protocols and tumor systems described in Geran et al., Cancer Chemother. Rep., Part 3, 3(No. 2), 1 (1972).
[b]Ip tumor implantation, ip QD1-9 treatment schedule.
[c]Subcutaneous tumor implantation, ip QD5-15 treatment schedule.
[d]mg/kg/injection.
[e]ILS = (treated survival ÷ control survival) × 100%]−100%.
[f]T − C = average weight change of test group minus average weight change of control animals in grams on day 5.
[g]T = toxic dose.

TABLE III

INTRACEREBRAL ANTITUMOR ACTIVITY[a] OF COMPOUND 9

| Ic L1210 lymphoid leukemia[b] | | | | Ic P388 lymphocytic leukemia[b] | | | | Ic ependymoblastoma[c] | | | | |
|---|---|---|---|---|---|---|---|---|---|---|---|---|
| Expt no. | Dose[d] | ILS[e] | T − C[f] | Expt no. | Dose | ILS | T − C | Expt no. | Dose | ILS | T − C | Cures[g] |
| 28 | 6.25 | 10 | −2.1 | 25 | 6.25 | T[h] | −2.1 | 133 | 4.00 | T | −3.0 |  |
|  | 3.12 | 84 | −1.1 |  | 3.12 | 39 | −0.1 |  | 2.00 | 349 | −1.3 | 4/6 |
|  | 1.56 | 51 | −0.6 |  | 1.56 | 37 | −0.6 |  | 1.00 | 348 | −1.3 | 3/6 |
|  | 0.78 | 16 | +0.5 |  | 0.78 | 27 | +1.0 |  |  |  |  |  |
|  |  |  |  |  | 0.39 | 7 | +0.8 |  |  |  |  |  |
| 29 | 6.25 | 3 | −2.8 | 26 | 6.25 | T | −2.8 | 136 | 8.00 | T | −5.0 |  |
|  | 3.12 | 79 | −2.1 |  | 3.12 | 31 | −2.1 |  | 4.00 | 276 | −2.4 | 4/6 |
|  | 1.56 | 46 | −0.5 |  | 1.56 | 51 | −1.1 |  | 2.00 | 277 | −1.1 | 5/6 |
|  | 0.78 | 3 | −0.5 |  | 0.78 | 25 | −0.4 |  | 1.00 | 126 | −0.2 | 1/6 |
|  |  |  |  |  | 0.39 | 2 | −0.7 |  |  |  |  |  |
|  |  |  |  |  |  |  |  | 144 | 4.00 | T | −3.9 |  |
|  |  |  |  |  |  |  |  |  | 2.00 | 171 | −2.7 | 5/6 |
|  |  |  |  |  |  |  |  |  | 1.00 | 171 | −2.1 | 5/6 |
|  |  |  |  |  |  |  |  |  | 0.50 | 62 | −1.8 |  |

TABLE III-continued
INTRACEREBRAL ANTITUMOR ACTIVITY[a] OF COMPOUND 9

| Ic L1210 lymphoid leukemia[b] | | | | Ic P388 lymphocytic leukemia[b] | | | | Ic ependymoblastoma[c] | | | |
|---|---|---|---|---|---|---|---|---|---|---|---|
| Expt no. | Dose[d] | ILS[e] | T − C[f] | Expt no. | Dose | ILS | T − C | Expt no. | Dose | ILS | T − C Cures[g] |
| | | | | | | | | | 0.25 | 30 | −1.5 |

[a]Protocols and tumor systems described in Geran et al., Cancer Chemother, Rep., Part 3, 3(No. 2), 1 (1972).
[b]Ic tumor implantation, ip QD1-9 treatment schedule.
[c]Ic tumor implantation, ip QD1-5 treatment schedule.
[d]mg/kg/injection.
[e]See Table II.
[f]T − C = average weight change of test group minus average weight change of control animals in grams on day 5.
[g]Number of animals alive per six test animals on day of termination of experiment (day 99 for expt 133 and day 60 for expt 136 and 144).
[h]Toxic dose.

TABLE IV
ANTITUMOR ACTIVITY OF COMPOUND 9[1]

| (IC) Ependymoblastoma[2] | | (IP) L1210 | | (IC) L1210 | | (IP) B16 | | (IP) P388 | | (IC) P388 | |
|---|---|---|---|---|---|---|---|---|---|---|---|
| OD[3] | % ILS | OD | % ILS | OD | % ILS | OD | % ILS | OD | % ILS | OD | % ILS |
| 2 | >277 (5)* | 3 | 169 | 3 | 84 | 3 | 94 | 1.6 | 138(1) | 1.5 | 51 |
| 1 | >202 (4) | 3 | 113 | 3 | 79 | 3 | 70 | 1.6 | 135 | 3 | 39 |
| 2 | >172 (6) | 2 | 101 | 5 | 63 | 3 | 62 | 0.8 | 112(1) | | |
| 1 | >171 (5) | 4 | 100 | 3 | 58 | | | | | | |

Notes:
[1]Treatment schedules are QD1-9 unless otherwise indicated
[2]QD1-5 treatment schedule
[3]mg/kg/injection
*Numbers in parentheses are survivors of 6 test mice on experiment termination day (EM-day 60; P388-day 30).

Because of its activity in the L1210 system, No. 9 was tested in some additional intraperitoneal (IP) and intracerebral (IC) transplanted mouse tumor models. Biological data are shown for the L1210 (QD1-9 schedule) and P388 leukemia systems plus the B16 melanocarcinoma and Lewis lung solid tumor systems in Table II. Central nervous system antitumor activity is given in Table III for the intracerebrally implanted L1210, P388, and ependymoblastoma tumor systems. The criterion for minimum activity is defined here as follows: intraperitoneal and intracerebral L1210 leukemia, 25%; intraperitoneal and intracerebral P388 leukemia, 25%; B16 melanoma, 40%; Lewis lung carcinoma, 25%; and intracerebral ependymoblastoma, 40%. A summary of significant antitumor data obtained with compound No. 9 is shown in Table IV.

The L1210, P388 and B16 test systems described in Table II utilize intraperitoneal (IP) tumor implantation and IP drug treatment while the Lewis lung system employs subcutaneous tumor implantation and IP treatment. All three CNS tumor models (Table III) use intracerebral (IC) tumor implantation and IP treatment.

Table II indicates that the diaziridinyldi(carboethoxyamino)benzoquinone, No. 9, has reproducible activity in excess of ILS 100% in the standard IP L1210 test on the QD1-9 treatment schedule. The optimum dose (OD) is 2-3 mg/kg and a therapeutic ratio (TR, highest active dose divided by lowest active dose) of approximately 4 is seen. Similar activity results were observed in the P388 system at a slightly lower OD (1-2 mg/kg). B16 melanoma activity was significant with activity as high as 70% observed at an OD of 3.12 mg/kg. Marginal activity was seen in the refractory Lewis lung tumor system. While insufficient low-dose testing was carried out to establish TI values in the last three systems, No. 9 might be characterized as a reasonably toxic material with a TR in the range of 3-4.

Antitumor activity was observed with compound No. 9 in all of the IC transplanted mouse tumor systems studied (Table III). While only two dose response experiments were conducted in the IC L1210 and IC P388 systems, reproducible activity was seen in both caes. The activity of No. 9 in IC L1210 (ILS 79, 84% at OD 3.12 mg/kg) is noteworthy.

A third IC transplanted mouse tumor model, the ependymoblastoma system, was also studied. This system requires intracerebral implantation of a solid tumor fragment while the IC L1210 and IC P388 systems utilize IC inoculated ascites tumor fluid. All three use IP drug treatment however. Compound No. 9 was very active in the ependymoblastoma IC tumor model. Cures (survivors from the group of six mice on the last day of the experiment) are indicated. Experiments 136 and 144 were terminated on day 60. Since the number of cures was about the same, the differences in T/C values in these two experiments reflect differences in the life span of the two different sets of control animals. Experiment 133 was terminated on day 99 with a resulting higher activity value. A majority of the test animals were alive on day 99 at a dose of 2.0 mg/kg in this experiment. An optimum dose of 1-2 mg/kg is indicated for No. 9 in the ependymoblastoma system with a TR of 4-8.

The inactivity of the other compounds studied here is also noteworthy. Methyl substitution in the aziridine ring (Nos. 10, 11, 21) abolished activity relative to No. 9 and a previously reported aziridinylacetylaminobenzoquinone. All ring-halogenated aziridinylquinones (Nos. 2-4, 15-17) were inactive. Although the diethylmercapto derivative No. 5 gave one marginally active test (ILS 30%, IP L1210, Q4D), the activity was not reproducible. The dipropylmercapto analog No. 6 was inactive. These results are in contrast with the activities found (ILS 50%) for the corresponding alkoxy aziridinylbenzoquinone compounds. When the aziridine rings of No. 9 were opened to the corresponding di (one arm mustard) derivative No. 12, activity was abolished.

In the compounds and test systems investigated here, the aziridine ring is necessary, but not sufficient, for antitumor activity. It has been theorized that the inactivity of the dihalodiaziridinyl compounds is due to either an electronic effect and resulting effect on the redox potential, a lipophilic transport effect, or a steric effect on the degree of coplanarity of the quinone and aziridine ring systems.

As previously discussed, a first approach utilized chloranil as a starting material and resulted in an aziridinyl quinone urethane derivative, compound No. 9, which was very active in the intraperitoneal leukemia L1210, leukemia P388, and the B16 melanoma test systems. In addition, substantial intracerebral (IC) L1210 and P388 activity was observed and the compound was curative in the murine ependymoblastoma brain tumor model. The solubility of this urethane derivative appeared to be adequate, Further investigations were initiated to produce the previously unevaluated diaziridinyl benzoquinone derivatives containing amino substituents in the other two available ring positions.

While 2,5-diaziridinyl-1,4-benzoquinone derivatives may be prepared in a number of ways, substitution reactions utilizing halo or alkoxy quinones have been most generally employed. Chloranil has been used extensively as a starting material for the preparation of 2,5-diaziridinyl-3,6-disubstituted-1,4-benzoquinones. Although the chlorine atoms in the 2-and 5-positions are readily replaced by nucleophiles, the electron donating properties of the added groups usually deactivate the ring toward replacement of the other two chlorine atoms. While compound 4, for example, as shown in Table V, is easily prepared from chloranil and ethylenimine, this compound and other diaminodichloro-p-benzoquinone derivatives undergo no further displacement reactions with amines. This is not the case, however, with the analogous difluoro analog, compound No. 32, which is prepared from tetrafluoro-1,4-benzoquinone, also known as fluoranil.

Reactions of this type are described, for example, by Finley, *Chemistry of Quinonoid Compounds*, Part 2, S. Patai, Ed., Wiley, N.Y., 1974, p. 1101; Wallenfals et al., *Angew. Chem.*, 70, 313 (1958); Wallenfals et al., *Ann.*, 667, 55 (1963); and Makarova et al., *Zhur. Obshch. Khim.*, 33, 1643 (1963). The two fluorine atoms of compound No. 32 are readily replaced by amines to form tetraamino-benzoquinone derivatives. This reaction was used as the synthetic method for the preparation of compounds Nos. 33–47, shown in Table VI. These agents were evaluated for their antitumor activity in a number of murine intraperitoneal and intracerebral transplanted mouse tumor systems.

TABLE V

23, $R_1 = R_2 = Cl$
24, $R_1 = R_2 = F$
25, $R_1 = F$; $R_2 = N\langle\text{-CH}_3$ 26, $R_1 = NHCH_3$; $R_2 = N\langle\text{-CH}_3$

9, $Y = Z = NHCOOC_2H_5$
27, $Y = Z = NHCOCH_3$
28, $Y = Z = OCH_3$

29, $Y = H$; $Z = N\triangleleft$

30, $Y = CH_3$; $Z = CH(OCH_3)CH_2OCONH_2$

TABLE V-continued

31, $Y = F$; $Z = N\langle\text{O}\rangle$

4, $Y = Z = Cl$
32, $Y = Z = F$

TABLE VI

33, $R = NH_2$
34, $R = NHCH_3$
35, $R = NHC_2H_5$
36, $R = NHC_3H_7$
37, $R = NHC_4H_9$
38, $R = NHCH_2CH_2OH$
39, $R = NHCH_2CH(OH)CH_2OH$
40, $R = NHCH_2CONH_2$
41, $R = N(CH_3)_2$
42, $R = N(CH_3)CH_2CH_2OH$
43, $R = N\langle\text{cyclobutyl}\rangle$
44, $R = N\langle\text{piperidine}\rangle$
45, $R = N\langle\text{piperidine-OH}\rangle$
46, $R = N\langle\text{morpholine}\rangle$
47, $R = N\langle\text{piperazine}\rangle N-CH_2CH_2OH$ Although several tetraamino-1,4-benzoquinone derivatives are known, only the tetraaziridinyl derivative appears to have been evaluated as an antitumor agent, and its activity in the L1210 leukemia system was only moderate (ILS 39%). The selection of the appropriate amino substituents for compounds 33–47 was important since they might influence both the biological transport properties and the chemical reactivity of the compounds. The partition coefficient, an important factor in determining the biological transport properties of a compound, was especially significant since this parameter also gives a rough guide to aqueous solubility properties which are important in this family of sparingly soluble compounds. The electronic properties of the R-group substituents (Table VI) should influence the redox potential of the quinone system. This factor is known or postulated to be an important factor in determining the antitumor activity in other quinone systems, including mitomycin C analogs and bioreductive alkylating agents. If the redox potential should be an important factor in the biological activity of the diaziridinyl-benzoquinones, the substitution of the other two available positions with alkylamino groups should produce a maximum effect in the parameter relative to other possible substituents. This would result in either a maximum or minimum in biological activity provided the activity is a linear function of the redox potential. The steric effects of the R-groups should influence the degree of co-planarity of the ethylenimine and quinone rings. This should affect the reactivity of the alkylating groups as well as the redox potential of the quinone. For these reasons, the compounds which were synthesized for antitumor evaluation were chosen with the intention of creating a spread in lipophilic ($\pi$) steric and electronic R-group effects.

Fluoranil reacted with ethylenimine to produce the key intermediate 2,5-diaziridinyl-3,6-difluoro-1,4-benzoquinone. Three isomers are possible from the disubstitution reaction and two have been previously isolated and identified. X-ray crystallographic analysis verified that compound No. 32 was the structure of the material used in our reactions. The colorless Konig's adducts sometimes found with $\beta$-hydroxyethylaminobenzoquinones were not observed with the tetraamino derivatives described here. The physical and chemical properties of these compounds are given in Table VII.

Two aziridinylbenzoquinones are presently undergoing laboratory studies. Trenimon, No. 29, is being studied mainly in Europe while carbazilquinone, No. 30, has had extensive investigation in Japan. Compounds Nos. 27 and 28 are representative of the amide and alkoxy analogs with intraperitoneal (IP) leukemia L1210 activity.

The urethane derivative, No. 9, has been found to have intracerebral (IC) as well as IP antitumor activity against transplanted mouse tumor test systems. In an attempt to determine the structural factors affecting the activity of the diaminodiaziridinyl analogs, the compounds Nos. 33–47 were prepared and evaluated in the IP murine L1210 lymphoid leukemia tumor model. When an IP L1210 test gave increase in life span (ILS) values greater than 50%, the compound was also tested in the IC L1210 model. Standard NCI protocols were used, as described, for example, in Cancer Chemother. Repts., Part 3, No. 2, 3, 1 (1972).

TABLE VII

PHYSICAL AND CHEMICAL PROPERTIES OF 2,5-DIAZIRIDINYL-3,6-DIAMINO-1,4-BENZOQUINONES

| Compound Number | Recrystallization Solvent[a] | Yield (%) | mp (° C.) | Color | $\lambda CH_3OH_{(log\epsilon)}$ max | Approx. $H_2O$ Sol. (mg/ml) | log $P^{[b]}$ | Mol formula | Analyses[f] |
|---|---|---|---|---|---|---|---|---|---|
| 26 | A | 84 | 179 | green | 369 (4.13) | <0.1 | | $C_{14}H_{20}N_4O_2$ | C,H,N |
| 31 | B | 51 | 157 | gray | 325 (3.88) | 2 | | $C_{14}H_{16}FN_3O_3$ | C,H,N,F |
| 33 | C | 73 | 220 | green | | <<0.1 | | $C_{10}H_{12}N_4O_2$ | C,H,N |
| 34 | A | 70 | 220 | green | 374 (4.16) | <0.1 | | $C_{12}H_{16}N_4O_2$ | C,H,N |
| 35 | A | 57 | 157 | green | 374 (4.20) | 0.5 | | $C_{14}H_{20}N_4O_2$ | C,H,N |
| 36 | A | 60 | 140 | green | 375 (4.17) | <0.1 | | $C_{16}H_{24}N_4O_2$ | C,H,N |
| 37 | C | 91 | 95 | green | 377 (4.12) | <0.1 | | $C_{18}H_{28}N_4O_2$ | C,H,N |
| 38 | A | 48 | 188 | green | 375 (4.08) | 2 | −1.48 | $C_{14}H_{20}N_4O_4$ | C,H,N |
| 39 | D | 77 | 273 | green | 365 (4.15) | 30 | −1.97 | $C_{16}H_{24}N_4O_6$ | C,H,N |
| 40 | D | 81 | 200 | green | 365 (3.72) | 0.5 | | $C_{14}H_{18}N_6O_4$ | C,H,N |
| 41 | E | 59 | 112 | green | 455 (3.72) 298 (3.77) | 10 | | $C_{14}H_{20}N_4O_2$ | C,H,N |
| 42 | F | 74 | 125 | green | 455 (3.67) 310 (3.71) | 60 | −0.38 | $C_{16}H_{24}N_4O_6$ | C,H,N |
| 43 | G | 64 | 160 | brown | 440 (3.80) 274 (3.65) | 0.5 | | $C_{18}H_{24}N_4O_6$ | C,H,N[c] |
| 44 | G | 62 | 180[d] | brown | 466 (3.80) 299 (3.80) | <0.1 | | $C_{20}H_{28}N_4O_2$ | C,H,N |
| 45 | G | 54 | 235 | red | 454 (3.69) 300 (3.72) | 1 | | $C_{20}H_{28}N_4O_4$ | C,H,N[e] |
| 46 | B | 28 | 224 | brown | 453 (3.20) 307 (3.42) | <0.1 | 0.52 | $C_{18}H_{24}N_4O_4$ | C,H,N |
| 47 | F | 64 | 170 | green | 452 (3.71) 297 (3.76) | 20 | −0.75 | $C_{22}H_{34}N_6O_4$ | C,H,N |

[a]A = ethanol, B = benzene, C = water wash, D = methanol wash, E = hexane, F = toluene, G = THF + hexane
[b]Octanol/$H_2O$ values determined by C. Hansch and M. Yamakawa, Pomona College.
[c]N calc., 17.06; found, 16.57
[d]lit. mp 177°
[e]N calc, 14.42; found, 13.95
[f]Found microanalytical values for the elements listed corresponded to calculated values within ±0.4%.

Aqueous saline solution (0.9%) was used as the drug vehicle. Normally, five doses were employed per experiment with the top dose chosen to produce toxicity. The lower doses were 50% of each preceeding dose.

Since this family of aminoaziridinyl-1,4-benzoquinones subsequently proved to have very good L1210 activity, the members were subjected to testing in two additional intraperitoneal systems, including P388 lymphocytic leukemia and B16 melanocarcinoma, as well as the murine ependymoblastoma brain tumor system. Intraperitoneal antitumor data are given in Tables VIII and IX. Table X lists the antitumor activity of this series against the intracerebrally implanted solid ependymoblastoma and ascites leukemia L1210 tumor systems. The criterion for minimum activity, %ILS, is defined here as follows: Intraperitoneal and intracerebral leukemia L1210 and intraperitoneal leukemia P388, 25%; intraperitoneal B16 melanoma and intracerebral ependymoblastoma, 40%. Consistent with NCI antitumor test protocols, intraperitoneal (IP) administration of the drug was employed with all five tumor systems investigated. Tumor implantation was IP in the systems designated IP leukemia L1210 and P388 as well as B16 melanoma. Intracerebral (IC) tumor implantation was utilized in the IC L1210 and ependymoblastoma tumor systems. Table XI lists those compounds with outstanding activity in two or more tumor systems.

The initial antitumor experiments were carried out in the IP L1210 system on the Q4D (day 1,5,9) treatment schedule. These experiments confirmed the L1210 activity in this series and established the proper dose ranges for the determination of any schedule dependency in the IP L1210 system (Table VIII).

TABLE VIII

INTRAPERITONEAL LYMPHOID LEUKEMIA L1210 ACTIVITY

| Comp. No. | QD1-9[a] | | | | Q4D(1,5,9)[b] | | | | Day 1[c] | | | |
|---|---|---|---|---|---|---|---|---|---|---|---|---|
| | Exp. No. | OD[d] | T−C[e] | ILS[f,g] | Exp. No. | OD | T−C | ILS | Exp. No. | OD | T−C | ILS |
| 26 | 7968 | 5.0 | −2.9 | 69 | 7691 | 12.5 | −1.8 | 93 | 8744 | 5.0 | −0.9 | 42 |
| | 7967 | 5.0 | −4.4 | 37 | 7982 | 12.5 | −2.4 | 52 | 8743 | 10.0 | −3.3 | 39 |
| 31 | 8769 | 6.0 | −3.5 | 29 | 8698 | 6.2 | −1.8 | 21 | 8757 | 12.5 | −3.2 | 21 |
| | 8770 | 1.5 | −0.2 | 11 | 8697 | 3.1 | −2.2 | 7 | 8758 | 6.2 | −3.3 | 4 |
| 33 | 8857 | 0.4 | −4.5 | 115 | 8546 | 0.5 | −1.7 | 161(3) | 8757 | 1.0 | −1.7 | 95 |
| | 8856 | 0.3 | −0.3 | 100 | 8769 | 0.02 | −2.8 | 124(2) | 8758 | 0.5 | −0.9 | 26 |
| 34 | 8343 | 0.2 | −1.6 | 73(1) | 8343 | 0.8 | −1.6 | 57 | 8744 | 0.7 | −3.4 | 34 |
| | 8004 | 0.2 | −2.5 | 61 | 7860 | 0.4 | −1.0 | 56 | 8743 | 0.7 | −2.8 | 19 |
| 35 | 8004 | 1.5 | −3.3 | 112(2) | 7860 | 3.0 | −2.3 | 75 | 8744 | 1.5 | −1.9 | 68 |
| | 8005 | 1.5 | −3.3 | 91(1) | 7861 | 1.5 | −1.8 | 57 | 8743 | 1.5 | −2.2 | 54 |
| 36 | 8005 | 6.2 | −2.9 | 48 | 7861 | 6.2 | −1.1 | 28 | 8743 | 12.0 | +0.2 | 41 |
| | 8004 | 6.2 | −2.4 | 43 | 7860 | 6.2 | −0.3 | 25 | 8744 | 1.5 | −0.1 | 17 |
| 37 | 8741 | 10.0 | −1.5 | 36 | 8663 | 12.5 | −1.4 | 44 | 8743 | 10.0 | −0.8 | 11 |
| | 8742 | 5.0 | −1.7 | 30 | 8727 | 8.2 | −2.9 | 25 | 8744 | 10.0 | −1.4 | 5 |
| 38 | 5178 | 0.7 | −3.2 | 205(2) | 7861 | 0.7 | −2.0 | 131 | 8647 | 1.5 | −3.8 | 175(5) |
| | 8005 | 0.7 | −3.0 | 134(3) | 7860 | 0.7 | −0.3 | 70 | 8743 | 1.5 | −3.4 | 119(3) |
| 39 | 8647 | 4.0 | −2.7 | 206(5) | 8450 | 4.0 | −0.3 | 90 | 8743 | 4.0 | −3.2 | 173(4) |
| | 8648 | 2.0 | −2.1 | 133(2) | 8454 | 8.0 | −2.0 | 79 | 8744 | 2.0 | −2.3 | 89 |
| 40 | 8861 | 10.0 | −4.9 | 92 | 8663 | 8.0 | −2.7 | 93 | 8743 | 10.0 | −1.6 | 21 |
| | 8742 | 10.0 | −2.7 | 91 | 8727 | 8.0 | −2.8 | 32 | 8744 | 10.0 | −1.8 | 15 |
| 41 | 8741 | 0.75 | −1.6 | 39 | 8740 | 3.0 | −0.4 | 120(1) | 8743 | 1.5 | +0.4 | 21 |
| | 8742 | 0.37 | 0.0 | 16 | 8656 | 3.0 | −1.0 | 73 | 8744 | 1.5 | −2.2 | 15 |
| 42 | 8742 | 1.5 | −2.4 | 114(1) | 8663 | 0.4 | −0.9 | 57 | 8744 | 1.0 | −0.9 | 26 |
| | 8826 | 1.5 | −3.6 | 111(1) | 8727 | 0.2 | +4.0 | 19 | 8743 | 0.2 | −2.6 | −5 |
| 43 | 8769 | 2.0 | −2.7 | 24 | 8698 | 6.2 | −2.3 | 43 | 8757 | 4.0 | −1.0 | 25 |
| | 8770 | 2.0 | −2.2 | 21 | | | | | 8758 | 2.0 | −0.9 | 8 |
| 44 | 8883 | 10.0 | −2.2 | 28 | 8739 | 35 | −2.4 | 26 | 8757 | 20.0 | −1.7 | 16 |
| | | | | | 8697 | 12.5 | −3.0 | 22 | 8758 | 80.0 | −2.7 | 8 |
| 45 | 8741 | 3.0 | −1.8 | 59 | 8727 | 6.0 | −3.8 | 104(2) | 8743 | 3.0 | −0.7 | 21 |
| | 8742 | 3.0 | −3.6 | 44 | 8663 | 4.0 | −2.5 | 84 | 8744 | 0.7 | −0.9 | 8 |
| 46 | 8769 | 6.0 | −5.7 | 64 | 8697 | 6.0 | −2.6 | 49 | 8757 | 12.5 | −3.0 | 42 |
| | 8770 | 1.5 | −2.7 | 32 | 8698 | 6.0 | −2.6 | 44 | 8758 | 3.1 | −1.6 | −14 |
| 47 | 8539 | 1.0 | −1.7 | 147 | 8320 | 4.0 | −2.1 | 180(3) | 8743 | 4.0 | −0.7 | 52 |
| | 8647 | 0.5 | −1.7 | 114(1) | 8739 | 2.0 | −1.5 | 165(4) | 8744 | 4.0 | −3.4 | 21 |

[a] Day 1-9 treatment schedule (9 injections)
[b] Day 1,5,9 treatment schedule (3 injections)
[c] Day 1 only treatment schedule (1 injection)
[d] Optimum dose (mg/kg/injection)
[e] Average weight change of test group minus average weight change of control group in grams on day 5.
[f] Percentage increase in life span of treated animals [(treated survival ÷ control survival) × 100%] − 100%
[g] Number of animals alive per 6 test animals on the day of termination of the experiment (L1210 and P388-day 30; B16 melanoma and ependymoblastoma-day 60)

TABLE IX

INTRAPERITONEAL LYMPHOCYTIC LEUKEMIA P388 AND B16 MELANOCARCINOMA ACTIVITY[a]

| Compound No. | Lymphocytic Leukemia P388 | | | | B16 Melanocarcinoma | | | |
|---|---|---|---|---|---|---|---|---|
| | Exp. No. | OD[b] | T − C | ILS | Exp. No. | OD | T − 0C | ILS |
| 26 | | | | | 301 | 5.0 | −1.0 | 70 |
| | | | | | 300 | 5.0 | −0.7 | 48 |
| 31 | 5282 | 3.0 | −2.3 | 57 | 302 | 0.7 | −0.3 | 18 |
| | 5281 | 6.0 | −2.5 | 54 | 303 | 0.7 | 0.0 | 9 |
| 33 | 5281 | 0.2 | −1.7 | 171(1) | 302 | 0.1 | −0.5 | 31 |
| | 5439 | 0.2 | −1.9 | 156 | 303 | 0.02 | −0.1 | 19 |
| 34 | 5112 | 0.2 | −3.6 | 95 | 301 | 0.4 | −0.7 | 39 |
| | 5111 | 0.1 | −3.3 | 69 | 294 | 0.05 | −3.1 | 29 |
| 35 | 4902 | 1.5 | −2.6 | 160 | 300 | 0.4 | −0.3 | 26 |
| | 4903 | 0.7 | −2.0 | 103 | 301 | 0.7 | −0.4 | 24 |
| 36 | 5111 | 6.0 | −3.0 | 151(2) | 288 | 5.0 | −0.5 | 36 |
| | 5112 | 6.0 | −3.3 | 108 | 287 | 5.0 | −2.9 | 32 |
| 37 | 5281 | 5.0 | −0.4 | 64 | 302 | 10.0 | −1.0 | 36 |
| | 5282 | 10.0 | −2.0 | 49 | 303 | 5.0 | −0.1 | 11 |
| 38 | 4903 | 0.4 | −2.6 | 175(3) | 288 | 0.4 | −0.6 | 61 |
| | 4902 | 0.4 | −2.3 | 160(2) | 287 | 0.4 | −2.7 | 51 |
| 39 | 5262 | 4.0 | −3.4 | 143(6) | 301 | 4.0 | −2.5 | 50 |
| | 5405 | 4.0 | −3.5 | 141(4) | 314 | 6.0 | −3.0 | 42 |
| 40 | 5281 | 2.0 | −2.3 | 85 | 302 | 8.0 | −1.4 | 37 |
| | 5282 | 2.0 | −1.1 | 71 | 303 | 0.5 | +0.5 | 22 |
| 41 | 5282 | 1.0 | −2.7 | 74 | 303 | 0.2 | +0.3 | 16 |
| | 5281 | 0.5 | −1.8 | 37 | 302 | 0.2 | −0.5 | 12 |
| 42 | 5439 | 1.6 | −2.4 | 162 | 302 | 0.8 | −2.3 | 47 |
| | 5440 | 0.8 | −2.7 | 145 | 303 | 0.8 | −1.2 | 31 |
| 43 | 5282 | 1.0 | −1.8 | 72 | 303 | 2.0 | +0.8 | 28 |
| | 5281 | 0.2 | −4.3 | 55 | 302 | 2.0 | −0.5 | 18 |
| 44 | 5525 | 5.0 | +2.3 | 46 | 317 | 5.0 | −1.5 | 21 |
| | 5526 | 10.0 | −1.5 | 77 | 316 | 2.5 | −2.3 | −3 |
| 45 | 5282 | 1.0 | −2.5 | 95 | 302 | 1.0 | −1.1 | 40 |
| | 5281 | 1.0 | −0.5 | 78 | 303 | 1.0 | −0.1 | 37 |
| 46 | 5525 | 0.5 | −0.1 | 52 | 302 | 1.5 | −1.8 | 24 |
| | 5281 | 0.7 | −0.4 | 48 | 303 | 0.7 | +1.0 | 17 |
| 47 | 5263 | 0.5 | −0.8 | 149(3) | 301 | 0.5 | −0.6 | 22 |

TABLE IX-continued

INTRAPERITONEAL LYMPHOCYTIC LEUKEMIA P388 AND B16 MELANOCARCINOMA ACTIVITY[a]

| Compound No. | Lymphocytic Leukemia P388 | | | | B16 Melanocarcinoma | | | |
|---|---|---|---|---|---|---|---|---|
| | Exp. No. | OD[b] | T − C | ILS | Exp. No. | OD | T − 0 C | ILS |
| | 5262 | 1.0 | −2.4 | 143(6) | 300 | 0.2 | +0.1 | 22 |

[a] QD1-9 treatment schedule
[b] See footnotes in Table VIII for definitions

TABLE X

INTRACEREBRAL ANTITUMOR ACTIVITY

| Compound No. | Ependymoblastoma[a] | | | | Lymphoid Leukemia L1210[b] | | | |
|---|---|---|---|---|---|---|---|---|
| | Exp. No. | OD[c] | T − C | ILS | Exp. No. | OD | T − C | ILS |
| 26 | 152 | 10.0 | −2.5 | 294(1) | 35 | 5.0 | −2.0 | 39 |
| | 153 | 5.0 | −1.9 | 143(1) | 36 | 10.0 | −1.3 | 25 |
| 31 | 169 | 0.8 | +0.1 | 49 | | | | |
| | 168 | 1.5 | −1.3 | 40 | | | | |
| 33 | 177 | 0.2 | −2.7 | 215(4) | 43 | 0.3 | 0.0 | 60 |
| | 155 | 0.2 | −2.0 | 177(6) | 42 | 0.3 | −1.0 | 59 |
| 34 | 174 | 0.2 | −1.5 | 219(5) | 38 | 0.4 | −0.3 | 68 |
| | 175 | 0.4 | −1.8 | 218(4) | 33 | 0.2 | +0.3 | 60 |
| 35 | 175 | 1.5 | −2.0 | 218(2) | 30 | 3.0 | −2.2 | 44 |
| | 174 | 1.5 | −2.3 | 187(2) | 31 | 3.0 | −1.8 | 40 |
| 36 | 152 | 10.0 | −1.9 | 259(2) | | | | |
| | 153 | 5.0 | −1.2 | 143(1) | | | | |
| 37 | 166 | 6.0 | −2.3 | 93 | | | | |
| | 165 | 3.0 | −0.3 | 46 | | | | |
| 38 | 152 | 1.5 | −3.0 | 83 | 43 | 0.75 | +0.4 | 57 |
| | 174 | 1.5 | −1.0 | 70 | 30 | 0.75 | −1.8 | 48 |
| 39 | 155 | 1.0 | −0.4 | 99(1) | 39 | 4.0 | −1.6 | 43 |
| | 156 | 4.0 | −3.3 | 53 | 40 | 4.0 | −1.0 | 41 |
| 40 | 166 | 2.0 | −3.2 | 64 | 42 | 2.5 | −1.5 | 16 |
| | 165 | 1.0 | −1.4 | 50 | 43 | 10.0 | −1.8 | 16 |
| 41 | 177 | 1.0 | −2.3 | 215(5) | 43 | 3.0 | −0.4 | 72[d] |
| | 176 | 0.5 | +0.4 | 190(4) | 42 | 3.0 | +0.1 | 56[d] |
| 42 | 166 | 0.4 | −1.6 | 84 | 43 | 4.0 | −0.7 | 45 |
| | 165 | 0.2 | −1.2 | 69 | 42 | 2.0 | 0.9 | 32 |
| 43 | 171 | 1.6 | −1.9 | 101 | | | | |
| | 170 | 3.1 | −1.4 | 47 | | | | |
| 44 | 171 | 6.2 | −2.4 | 68 | | | | |
| | 170 | 12.5 | −3.1 | 46 | | | | |
| 45 | 165 | 0.5 | −1.2 | 64 | 43 | 8.0 | −0.3 | 30[d] |
| | 166 | 2.0 | −4.6 | 48 | 42 | 6.0 | −1.0 | 14[d] |
| 46 | 168 | 1.5 | −1.8 | 134 | | | | |
| | 169 | 0.4 | +0.8 | 82 | | | | |
| 47 | 155 | 1.0 | −1.2 | 75 | 39 | 2.0 | −1.4 | 43 |
| | 174 | 1.0 | −3.0 | 75 | 41 | 1.5 | −1.4 | 41 |

[a] QD1-5 treatment schedule
[b] QD1-9 treatment schedule unless otherwise indicated
[c] See footnotes Table VIII for definitions
[d] Q4D(1,5,9) treatment schedule

TABLE XI.

AZIRIDINYLBENZOQUINONES WITH OUTSTANDING ACTIVITY IN TWO OR MORE TUMOR SYSTEMS

| Compound No. | ILS (%) | | | | |
|---|---|---|---|---|---|
| | IP L1210 | P388 | B16 | IC L1210 | EM |
| 26 | | | 70 | | 294(1) |
| 9 | 169 | 138(1) | 70 | 84 | 277(5) |
| 33 | 161(3) | 171(1) | | 60 | 177(6) |
| 34 | | | | 68 | 219(5) |
| 35 | 112(2) | 160 | | | 218(2) |
| 36 | | 151(2) | | | 259(2) |
| 38 | 205(2) | 175(3) | 61 | 57 | |
| 39 | 206(5) | 143(6) | 50 | | 99(1)* |
| 41 | 120(1) | | | 72 | 215(5) |
| 42 | 114(1) | 162 | | | |
| 47 | 180(3) | 143(3) | | | |

*Repeat tests gave ILS values of 186(6) and 53%

The chronic (QD1-9) treatment schedule was found to be superior for almost all the compounds studied. Significant activity was obtained for all the diaziridinyl derivatives except the pyrrolidino, No. 43, and piperidino, No. 44, compounds. Some of the data variation may be attributable to the problem of reproducibly injecting suspensions of the more insoluble compounds.

Superior activity was obtained with several derivatives among which the dihydroxypropylamino and hydroxyethylamino compounds were outstanding with maximum ILS values in excess of 200% being observed. The theoretical maximum ILS values in a fully acceptable experiment ranges between 173 and 275% consistent with the control animal death limits set at 8 to 11 days and experiment termination on day 30. Multiple cures, defined as survivors on day 30 in the L1210 system, were observed for both compounds. Excellent activity was also observed with compounds Nos. 38 and 39 on the day 1 and Q4D treatment schedules. The day 1 schedule was generally the poorest of the three studied. Several compounds showed maximum activity with intermittent (Q4D) treatment.

Excellent activity was observed in the leukemia P388 system on the chronic treatment schedule (Table IX). Again, compounds 38, 39 and 47 were very active producing multiple cures (30 day survivors). As might be expected, compounds with outstanding L1210 activity usually possessed excellent P388 activity (Table XI). All the compounds studied in this series (Table IX) were active against leukemia P388, including the monoaziridinyl derivative, No. 31.

Only three compounds in the series were reproducibly active in the B16 melanoma tumor model (Table IX). Once again Nos. 38 and 39 proved active as did the 2'-methylaziridinyl analog, No. 26. The aziridinyl analog of No. 26 (No. 34) approached minimal reproducible activity as did No. 42, the N-methyl derivative of No. 38, and the 3'-hydroxypiperidino analog, No. 45.

Table X shows the data obtained in the intracerebrally implanted tumor systems. Only those compounds which had given L1210 intraperitoneal ILS values greater than 50% were tested in the intracerebral L1210 system. While nine of eleven compounds tested were reproducibly active, the parent amino compound (No. 33), and mono-(No. 34) and dimethylamino (No. 41) analogs were the most active against IC L1210 leukemia. Compounds Nos. 38, 39 and 47 which produced cures in the IP L1210 model gave activity levels which may be consistent with the inhibition of systemic disease produced by migration of L1210 cells from the implant site. The marginal IC L1210 activity associated with these three compounds, which produce long term survivors in the IP system, may be related to their hydrophilic nature, considering the log P values in Table VII, and a reduced ability to cross the blood-brain barrier.

All of the compounds in this study were reproducibly active against the ependymoblastoma or EM murine brain tumor system. It is probably more useful to compare cures, in terms of 60 day survivors, rather than ILS values in the EM model, since the ILS for a highly active compound is very dependent on the life span of the control animals which normally ranges from 17-21 days. The best IC L1210 active derivatives (Nos. 33, 34 and 41) were again among the most active materials against the EM tumor system. The ethyl-(No. 34) and propylamino (No. 36) compounds and the 2'-methylaziridinyl analog of No. 34 (compound 26) were also highly active. The hydrophilic dihydroxypropylamino compound (No. 39), which was curative in the IP L1210 and P388 leukemia systems, was active but gave a large spread in ILS values (53–186%). For this reason, No. 39 should be considered to have moderate to good EM activity. Again, its hydrophilic character may present transport problems in this IC tumor system. It is noteworthy that the majority of the most active compounds in the EM system are the simple monoalkylamino derivatives and their parent amine (No. 33).

Thus it is seen that several general points can be made about the diaminodiaziridinylbenzoquinone family. Its members have good antitumor activity against transplanted mouse tumor test systems, usually in several tumor systems. They are very potent with most optimum doses in the 0.1 to 5.0 mg/kg range on a chronic administration schedule. Therapeutic ratios (highest active dose divided by lowest active dose) were somewhat dependent upon the tumor system. For the most active compounds, therapeutic ratios averaged 4, 8 and 2 in IP L1210, P388 and B16 melanoma, respectively. These values were approximately 2 and 8 in the IC L1210 and ependymoblastoma tumor systems. These compounds are alkylating agents giving a positive 4-(p-nitrobenzyl) pyridine (NBP) test.

Several qualitiative structure-activity relationships are apparent. The compounds that are most active in the IP ascites tumor systems are the most polar, water soluble derivatives (Nos. 38, 39, 47). The parent amino compound No. 33, however, is also active and is so insoluble in any solvent that an ultraviolet spectrum was nonattainable. Among the monoalkylamines, activity appears to peak with the ethyl derivative (No. 35) in the L1210 series. A significant reduction in activity is noted for the propyl (No. 36) and butyl (No. 37) analogs. Leukemia P388 is usually a more sensitive system than L1210. In this series, however, L1210 activities were often equal to or greater than P388 values with the same compounds active against both tumors. Multiple cures were obtained in both systems.

Although several derivatives possess substantial reproducible B16 melanoma activity, this tumor is the most refractory of those studied in this investigation. The relationship between outstanding ascites tumor activity and B16 activity for Nos. 38 and 39 (Table XI) does not hold for several other compounds (Nos. 26, 47).

In the intracerebral systems, the trend toward activity with the more lipophilic compounds is apparent. The propyl derivative (No. 36) is still very active in the EM system and even the butyl analog has activity. These two groups greatly reduced L1210 activity relative to their lower carbon number congeners. Exceptionally high IP L1210 activity does not guarantee good activity in the IC L1210 system (Nos. 35, 42, 47). The significant activity of the parent compound (No. 33) as well as its methyl (No. 34) and dimethyl (No. 41) derivatives in the normally refractory IC L1210 system is noteworthy. The polar, water soluble compounds were generally less active in the EM system than the nonhydroxylated derivatives.

A comparison of activity in all tumor systems (Table XI) shows that those compounds which are best in the IP systems are not the most active in the IC systems. The dihydroxypropylamino analog (No. 39, which gives multiple long term survivors against the leukemia L1210 and P388 tumors is probably the most active compound in the IP ascites systems. The hydroxyethylamino Nos. 38 and 47 are also superior in these systems. In the EM system, the unsubstituted amino compond No. 33, and several alkylamino analogs (Nos. 34, 35, 36 and 41) are most active. The ethylcarbamate derivative, No. 9, is included in Table XI for comparison. While this compound does not give multiple cures in the ascites systems, it is curative in the EM system and has very substantial activity in all the other tumor systems studied. The high activity of the insoluble amino derivative No. 33 suggests the possibility that No. 33 might be the active agent and that the urethane 9 and the various active acylamino derivatives, such as No. 27, serve as solubiity enhancing groups which facilitate drug transport to the tumor cell and then produce No. 33 by hydrolysis. There is, however, no evidence for this at the present time.

Since retention of CNS antitumor activity with an improvement in water solublity by the use of non-ionic hydrophilic groups was a major objective of this investigation, a comment regarding the water solubilities and partition coefficients of the diaziridinylbenzoquinones (Table VII) is in order. The unsubstituted, parent amino derivative (No. 33) is an exceptionally insoluble material, not only in water, but in all solvents studied. The monoalkylamino compounds also have very limited water solubility. The addition of a second alkyl group (e.g., No. 41 vs No. 34) which might be expected to lower water solubility, actually increases the solubility greatly. This effect is also apparent in a comparison of No. 42 and No. 38. In both of these cases a dramatic decrease in melting point takes place upon addition of the second alkyl, in this case methyl, group. The increase in water solubility, therefore, may be due to a decrease in hydrogen bonding properties and a resulting decrease in the crystal forces in the solid state.

The partition coefficients of a few of these compounds were determined (Table VII). Initial calculated approximations of the partition coefficients in this series were made using the log P value of p-benzoquinone and substituent pi values in order to help determine which molecules to synthesize. The values measured after synthesis were qualitatively in the right order but contained large quantitative differences. This was expected because attempts to calculate known quinone partition coefficients values from a parent quinone plus pi values produced very poor results.

The partition coefficient of No. 9 was measured and found to have a log P value of 0.05. The water solubility of No. 9 is about 0.5 mg/ml. A comparison of log P values and water solubilities (Table VII) shows that a general qualitative correspondence between hydrophilicity and water solubility exists. However, no quantitative relationship between the two is apparent for the five derivatives with log P values.

In the following examples, all melting points are uncorrected and were recorded on a Thomas-Hoover capillary melting point apparatus. Elemental analyses were performed by NIAMDD, NIH, Bethesda, Maryland. Fluoranil, ethyleneimine and 2l-methylethyleneimine were obtained commercially. When several compounds were prepared by comparable procedures, only one representative example is included. New compounds were identified by nmr and ir spectroscopy. In the tetraamino derivatives, the methylene protons of the aziridine rings usually occurred as a singlet at $\delta 2.0$–$2.2$ in $CDCl_3$ or $DMSO$-$d_6$. This absorption appeared at $\delta 2.40$ ($CDCl_3$) for compound 11. Carbonyl absorption frequencies (nujol mull) occurred in the range 1620–1640 $cm^{-1}$ for the tetraamino compounds. Satisfactory elemental analyses (+0.4% of calculated values) are indicated by elemental symbols in Table VII. Room temperature water solubilities were determined by the incremental addition (pipet) of water to a weighed amount of compound with shaking. The solubility values in Table VII must be considered as approximate.

2,5-Diaziridinyl-3,6-difluoro-1,4-benzoquinone (32, (General procedure for 25). A solution of ethyleneimine (33.3 g, 0.77 mol) in dry tetrahydrofuran (100 ml) was added dropwise to a stirred solution of fluoranil (25.0 g, 0.14 mol) in tetrahydrofuran (100 ml) cooled by an ice water bath. The cold solution was stirred for 40 min, cold water (100 ml) was added. The precipitate was filtered, washed thoroughly with water and dried. Recrystallization from toluene gave 19.4 g (62%) of red crystals, mp 220° (lit. mp 230°, 212°).

2,5-Dizairidinyl-3,6-diamino-1,4-benzoquinone (33 ). A solution of compound 32 (0.56 g, 2.5 mmol) in tetrahydrofuran (100 ml) was saturated with dry ammonia gas at 2°. This solution was transferred to a pressure bottle and was heated overnight at 50°–55°. After cooling to room temperature, the bottle was opened carefully. The precipitate was filtered, washed with water, and dried to give 0.40 g (73%) of green crystals, mp 220°.

2,5-Diaziridinyl-3,6-bis(ethylamino)-1,4-benzoquinone (35) (General procedure for 26, 34, 36–40, 42, 44, 45). Anhydrous ethylamine (25 ml, 17.3 g, 380 mmol) was added to a stirred ice cold solution of compound 32 (2.0 g, 9 mmol) in 600 ml of tetrahydrofuran (methylamine used in the preparation of compound 34 was a 40% aqueous solution). The reaction mixture was stirred at 2° for 2 hr and then at 23° for 80 hr. Evaporation of the solvent in vacuo gave a dark green solid which was washed with ice water and dried in vacuo over KOH pellets. Recrystallization from ethanol gave 1.40 g (57%) of dark green prisms, mp 156°–157°.

2,5-Diaziridinyl-3,6-bis(dimethylamino)-1,4-benzoquinone (41). Dimethylamine hydrochloride (16.3 g, 0.2 mol) was slowly added to a stirred ice cold methanolic sodium methoxide solution (4.6 g, 0.2 mol Na in 100 ml methanol). The resulting mixture was stirred at room temperature for 0.5 hr and a solution of compound 32 (1.13 g, 0.005 mol) in tetrahydrofuran (300 ml) was added. The reaction mixture was stirred overnight at ambient temperature. The solvent was evaporated in vacuo to give a dark solid which was extracted with benzene. The solid obtained from evaporation of the benzene was recrystallized from hexane to give 1.1 g (59%) of green solid, mp 110°–112°.

2,5-Diaziridinyl-3,6-dipyrrolidino-1,4-benzoquinone (43). Compound No. 32 (1.13 g, 5 mmol) and pyrrolidine (2.0 ml, 1.7 g, 24 mmole) were added to benzene (250 ml) and the mixture was stirred at 23° for 3 days. The dark solution was heated to 50°–60° for 2 hr. The resulting precipitate was filtered and discarded. The filtrate was concentrated to give a brown solid which was recrystallized from tetrahydrofuran/hexane to give 1.05 g (64%) of brown product, mp 160°.

2,5-Diaziridinyl-3,6-dimorpholino-1,4-benzoquinone (46) and 2,5-diaziridinyl-3-fluoro-5-morpholino-1,4-benzoquinone (3). Morpholine (1.75 g, 20 mmol) was added to an ambient solution of compound 32 (1.13 g, 5 mmol) in tetrahydrofuran (250 ml). After stirring overnight, the solvent was removed in vacuo. The solid was washed with water, and recrystallized from benzene to give 0.50 g of compound 46 as a brown solid, (28%) mp 224°. Addition of the recrystallization filtrate to hexane gave 0.75 g (51%) of gray compound 31, mp 157°.

It is thought that the invention and many of its attendant advantages will be understood from the foregoing description, and it will be apparent that various changes may be made in the method described without departing from the spirit and scope of the invention or sacrificing its material advantages, the forms hereinbefore described being merely the preferred embodiments thereof.

It is claimed:

1. A method of treating transplanted tumors in mice comprising administering to a tumor-bearing mouse an antitumorically effective amount of the compound 2,5-diaziridinyl-3,6-bis (carboethoxyamino)-1,4-benzoquinone.

2. The method of claim 1 wherein said tumor is selected from the group consisting of L1210 lymphoid leukemia, P388 lymphocytic leukemia, B16 melanocarcinoma and Lewis lung carcinoma and wherein intraperitoneal treatment with said compound is employed.

3. The method of claim 1 wherein said tumor is selected from the group consisting of intracerebral L1210 lymphoid leukemia, intracerebral P388 lymphocytic leukemia and intracerebral ependymoblastoma and wherein intraperitoneal treatment with said compound is employed.

4. A method of treating transplanted tumors in mice comprising administering to a tumor-bearing mouse an antitumorically effective amount of the compound 2,5-di(2-methylaziridinyl)-3,6-bis(methylamino)-1,4-benzoquinone.

5. The method of claim 4 wherein said tumor is selected from the group consisting of intracerebral ependymoblastoma, L1210 lymphoid leukemia, intracerebral L1210 lymphoid leukemia and B16 melanocarcinoma.

6. A method of treating transplanted tumors in mice comprising administering to a tumor-bearing mouse an antitumorically effective amount of the compound 2,5-diaziridinyl-3,6-diamino-1,4-benzoquinone.

7. The method of claim 6 wherein said tumor is selected from the group consisting of intracerebral ependymoblastoma, L1210 lymphoid leukemia, intracerebral L1210 lymphoid leukemia and P388 lymphocytic leukemia.

8. A method of treating transplanted tumors in mice comprising administering to a tumor-bearing mouse an antitumorically effective amount of the compound 2,5-diaziridinyl-3,6-bis(methylamino)-1,4-benzoquinone.

9. The method of claim 8 wherein said tumor is selected from the group consisting of intracerebral ependymoblastoma, L1210 lymphoid leukemia, intracerebral L1210 lymphoid leukemia and P388 lymphocytic leukemia.

10. A method of treating transplanted tumors in mice comprising administering to a tumor-bearing mouse an antitumorically effective amount of the compound 2,5-diaziridinyl-3,6-bis(ethylamino)-1,4-benzoquinone.

11. The method of claim 10 wherein said tumor is selected from the group consisting of intracerebral ependymoblastoma, L1210 lymphoid leukemia, intracerebral L1210 lymphoid leukemia and P388 lymphocytic leukemia.

12. A method of treating transplanted tumors in mice comprising administering to a tumor-bearing mouse an antitumorically effective amount of the compound 2,5-diaziridinyl-3,6-bis(propylamino)-1,4-benzoquinone.

13. The method of claim 12 wherein said tumor is selected from the group consisting of intracerebral ependymoblastoma, L1210 lymphoid leukemia and P388 lymphocytic leukemia.

14. A method of treating transplanted tumors in mice comprising administering to a tumor-bearing mouse an antitumorically effective amount of the compound 2,5-diaziridinyl-3,6-bis(butylamino)-1,4-benzoquinone.

15. The method of claim 14 wherein said tumor is selected from the group consisting of intracerebral ependymoblastoma, L1210 lymphoid leukemia and P388 lymphocytic leukemia.

16. A method of treating transplanted tumors in mice comprising administering to a tumor-bearing mouse an antitumorically effective amount of the compound 2,5-diaziridinyl-3,6-bis(hydroxyethylamino)-1,4-benzoquinone.

17. The method of claim 16 wherein said tumor is selected from the group consisting of intracerebral ependymoblastoma, L1210 lymphoid leukemia, intracerebral L1210 lymphoid leukemia, P388 lymphocytic leukemia and B16 melanocarcinoma.

18. A method of treating transplanted tumors in mice comprising administering to a tumor-bearing mouse an antitumorically effective amount of the compound 2,5-diaziridinyl-3,6-bis(dihydroxypropylamino)-1,4-benzoquinone.

19. The method of claim 18 wherein said tumor is selected from the group consisting of intracerebral ependymoblastoma, L1210 lymphoid leukemia, intracerebral L1210 lymphoid leukemia, P388 lymphocytic leukemia and B16 melanocarcinoma.

20. A method of treating transplanted tumors in mice comprising administering to a tumor-bearing mouse an antitumorically effective amount of the compound 2,5-diaziridinyl-3,6-bis(glycineamido)-1,4-benzoquinone.

21. The method of claim 20 wherein said tumor is selected from the group consisting of intracerebral ependymoblastoma, L1210 lymphoid leukemia and P388 lymphocytic leukemia.

22. A method of treating transplanted tumors in mice comprising administering to a tumor-bearing mouse an antitumorically effective amount of the compound 2,5-diaziridinyl-3,6-bis(dimethylamino)-1,4-benzoquinone.

23. The method of claim 22 wherein said tumor is selected from the group consisting of intracerebral ependymoblastoma, L1210 lymphoid leukemia, intracerebral L1210 lymphoid leukemia and P388 lymphocytic leukemia.

24. A method of treating transplanted tumors in mice comprising administering to a tumor-bearing mouse an antitumorically effective amount of the compound 2,5-diaziridinyl-3,6-bis(N-methyl-N-hydroxyethylamino)-1,4-benzoquinone.

25. The method of claim 24 wherein said tumor is selected from the group consisting of intracerebral ependymoblastoma, L1210 lymphoid leukemia, intracerebral L1210 lymphoid leukemia and P388 lymphocytic leukemia.

* * * * *